(12) United States Patent
Navis

(10) Patent No.: US 6,889,713 B2
(45) Date of Patent: May 10, 2005

(54) PERITONEAL DIALYSIS CATHETER

(76) Inventor: John A. Navis, 43 Crestview Dr., Oswego, IL (US) 60543

(*) Notice: Subject to any disclaimer, the term of this patent is extended or adjusted under 35 U.S.C. 154(b) by 0 days.

(21) Appl. No.: 10/728,725

(22) Filed: Dec. 5, 2003

(65) Prior Publication Data

US 2004/0159360 A1 Aug. 19, 2004

Related U.S. Application Data

(63) Continuation-in-part of application No. 09/811,340, filed on Mar. 16, 2001, now Pat. No. 6,659,134.

(51) Int. Cl.⁷ ................................................ F16L 11/00
(52) U.S. Cl. ..................... 138/116; 138/117; 604/29; 604/27; 604/43; 604/93.01; 604/264; 604/284
(58) Field of Search .................. 138/114–117; 604/284, 604/523, 27, 29, 264, 43, 93.01

(56) References Cited

U.S. PATENT DOCUMENTS

| | | | | |
|---|---|---|---|---|
| 2,210,744 A | * | 8/1940 | Winder .................. 128/207.15 |
| 4,086,937 A | * | 5/1978 | Hechler, IV ................ 137/559 |
| 4,406,656 A | * | 9/1983 | Hattler et al. ............... 604/523 |
| 4,513,601 A | * | 4/1985 | Herbulot ...................... 72/398 |
| 5,059,170 A | * | 10/1991 | Cameron ...................... 604/43 |
| 5,334,139 A | * | 8/1994 | Jeppsson et al. .............. 604/28 |
| 5,695,457 A | * | 12/1997 | St. Goar et al. ........... 604/4.01 |
| 5,947,953 A | * | 9/1999 | Ash et al. .................... 604/508 |
| 6,409,699 B1 | * | 6/2002 | Ash ............................. 604/29 |
| 6,475,207 B1 | * | 11/2002 | Maginot et al. ............ 604/508 |
| 6,659,134 B2 | * | 12/2003 | Navis ......................... 138/116 |

* cited by examiner

Primary Examiner—James Hook
(74) Attorney, Agent, or Firm—David G. Henry

(57) ABSTRACT

A peritoneal dialysis catheter having an inflow conduit and an outflow conduit. Each conduits are linearly mated and contoured to cooperatively define a substantially circular cross sectional profile along a medial, trans-abdominal segment, but separating perhaps in radial fashion on either end of the medial, trans-abdominal segment, on a distal end to join fluted fluid transport branches and on proximal ends to join fittings for fluid delivery and collection external of the patient.

2 Claims, 3 Drawing Sheets (SECTION C-C)

(SECTION C-C)

(SECTION A-A)

(SECTION B-B)

(SECTION E-E)

(SECTION F-F)

(SECTION J-J)

(SECTION K-K)

PERITONEAL DIALYSIS CATHETER

CITATION TO PRIOR APPLICATION

This is a continuation-in-part application with respect to U.S. application Ser. No. 09/811,340 filed Mar. 16, 2001 now U.S. Pat. No. 6,659,134, from which priority is claimed pursuant to 35 U.S.C. 120.

BACKGROUND OF THE INVENTION

1. Field of the Invention

The present invention relates to medical catheters and to peritoneal dialysis catheters in particular.

2. Background Information

The foldable peritoneal dialysis catheter as disclosed in U.S. Pat. No. 5,322,519 ("the Ash catheter") represented a substantial advance in peritoneal catheter design and technology. However, the design of the ash catheter leaves certain characteristics of the ideal peritoneal dialysis catheter lacking.

The only feasible embodiments of the Ash catheter invention are those designed for inflow or outflow, but not both. Ash does teach the basic concept of a peritoneal dialysis catheter for continuous use (Column 4, lines 54 et seq.), in other words, one which includes separate conduits for simultaneous inflow and outflow. However, Ash fails to provide an actual, workable design.

Ash's FIG. 4 depicts a proposed design for a continuous use peritoneal catheter, but one which simply cannot be made when existing technology is applied to the silicone material from which such catheters must be made. For example, Ash's septum 128 must, in order to be operative, form a fluid seal with the inner wall of housing 122. Even if this were possible to achieve in the manufacturing process (which experts in the silicone extrusion and manufacturing industry indicate it is not), the resulting catheter would be too rigid (because of the added rigidity of such 128) to be suitable for implantation. In addition, the T-configuration shown for this embodiment would, in actual application, cause accumulation of biological debris (and ultimately clogging) at the 90 degree bends in the conduits. In addition the "double D" cross section configuration proposed by the Ash patent further precludes necessary catheter function. Such a cross section will occlude due to fiber at the 90 degree joint of the "T" junction.

Ash's alternative continuous dialysis catheter design (shown in Ash's FIG. 8) is also a non-viable design suggestion. Merely conjoining two parallel conduits (Ash's "plenum chambers" 146 and 148) creates a cross-sectional footprint (other than substantially circular) which is not suitable for passage through, and long-term residence in the abdominal wall because of increased propensity for leakage, bacterial invasion, etc.

It would well serve those who administer and those who receive peritoneal dialysis to provide a viable design for a continuous use peritoneal dialysis catheter—one which provides all the benefits of the viable embodiments of the Ash single direction flow catheter, but goes farther in satisfying the remaining, unfulfilled objectives for an Ash-like catheter for continuous dialysis use.

SUMMARY OF THE INVENTION

It is an object of the present invention to provide an improved peritoneal dialysis catheter.

It is another object of the present invention to provide an improved peritoneal dialysis catheter which is suitable for continuous use (allowing simultaneous inflow and outflow).

It is another object of the present invention to provide an improved peritoneal dialysis catheter which is suitable for continuous use, and which is of a design which can feasiblely be manufactured using available manufacturing technology and methods.

It is another object of the present invention to provide an improved peritoneal dialysis catheter which is suitable for continuous use, it presents an ideal, circular cross-sectional contour of portions of such catheter as pass through and reside in the abdominal wall of a recipient.

It is another object of the present invention to provide an improved peritoneal dialysis catheter which is suitable for continuous use, and which is of a design which minimizes the chances of conduit occlusion because of highly angular diversions of the conduits.

In satisfaction of these and related objects, the present invention provides an improved peritoneal dialysis catheter which, because of seemingly minor, but highly significant modifications from prior art designs, is unique in its manufacturerability and its capacity to serve as a continuous use peritoneal dialysis catheter without undue patient complications.

The peritoneal dialysis catheter design of the present invention, in the preferred embodiments, utilizes linearly mated conduits for that portion of the catheter which passes through the patient's abdominal wall (the trans-abdominal segment) and which cooperatively defines a substantially circular cross-sectional footprint. This feature provides the optimum cross-sectional footprint for lessening the likelihood of leakage and infection. Also, the present design avoids using a T-joint configuration as the transition from the trans-abdominal wall segment of the catheter to the peripheral fluid transport branches which reside within a patient's abdomen—such a T-joint configuration creating a propensity for clogging near the angular conduit deviations, as well as creating excessive bulk which impedes implantation.

The design of the present invention utilizes a J-joint configuration for at least one of the two intra abdominal branches of the present catheter at the transition from the trans-abdominal wall segment to the peripheral fluid transport branches. In this embodiment, the fluids follow a radial path as opposed to traversing a 90 degree bend; as such, fiber build-up or occlusion is avoided.

Further, the design of the present invention, because of the nested conduit design which lacks a septum as taught by Ash, is capable of actual manufacture, allows for the aforementioned circular cross-section for the trans-abdominal wall segment, and permits the transition from the trans-abdominal wall segment to the fluid transport branches of the catheter to proceed along a non-angular path.

DETAILED DESCRIPTION OF THE PREFERRED EMBODIMENT

Figure 1:
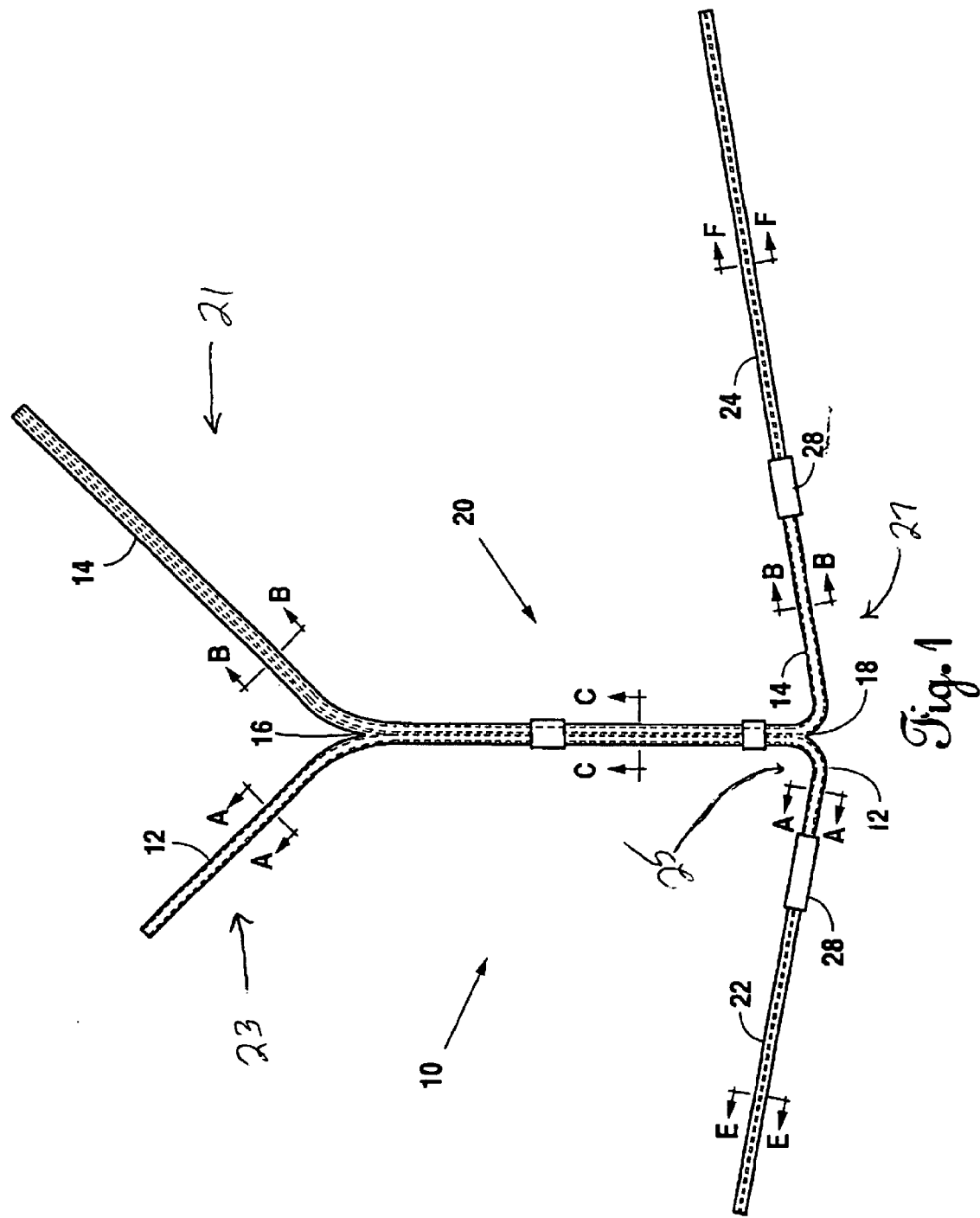
FIG. 1 is an elevational view of a preferred embodiment of the peritoneal dialysis catheter of the present invention.

Referring to FIG. 1, a peritoneal catheter of the present invention is identified generally by the reference numeral 10. Peritoneal catheter 10 comprises, generally, an inflow conduit 12 and an outflow conduit 14.

In the embodiment shown in FIG. 1, at a proximal divergence point 16, proximal from which is proximal segments 21 and 23, inflow conduit 12 and outflow conduit 14 are not attached and extend to respective sources of fluids to be infused or receptacles for fluids expelled in the peritoneal dialysis process. In another embodiment, equally as good but not shown in the figures, inflow conduit 12 and outflow conduit 14 remain bonded proximal from divergence point 16. At a distal divergence point 18, distal from which is distal segments 25 and 27, inflow conduit 12 and outflow conduit 14 diverge as they respectively extend toward junctures with fluid transport branches 22 and 24.

In the shown embodiment FIG. 1, between proximal divergence point 16 and distal divergence point 18 is a trans-abdominal segment 20 of catheter 10. The trans-abdominal segment 20 of catheter 10 is a length throughout which inflow conduit 12 and outflow conduit 14 are conjoined.

Figure 2:
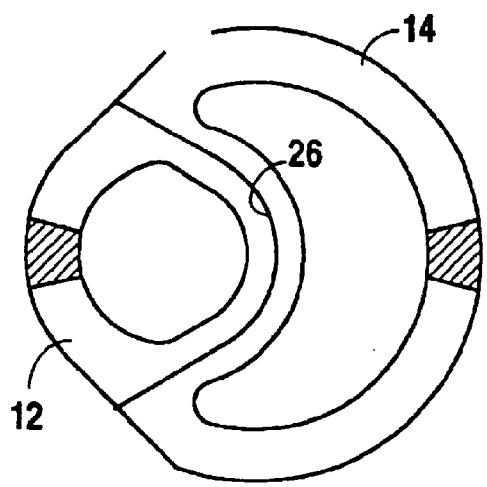
FIG. 2 is an elevational cross-section view of the catheter of FIG. 1 along line C—C of FIG. 1.
Figure 3:
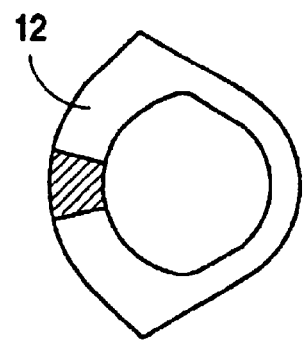
FIG. 3 is an elevational cross-section view of input conduit 12 shown along line A—A of FIG. 1.
Figure 4:
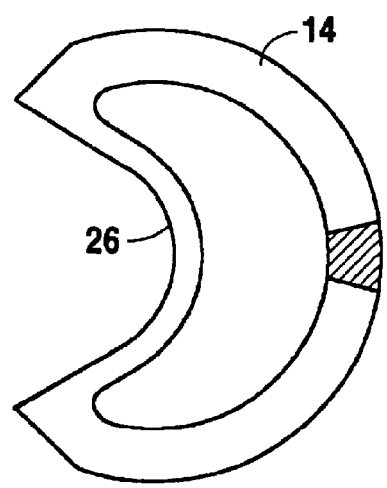
FIG. 4 is an elevational cross-section view of output conduit 14 shown along line B—B of FIG. 1.

Referring principally to FIGS. 2, 3, and 4, the respective cross-sectional shapes of inflow conduit 12 and outflow conduit 14, while they may vary from that shown in the preferred embodiment, should, when mated along the length of trans-abdominal segment 20 or proximal segments 21 and 23, cooperatively define a substantially circular cross-section for both conduits 12 and 14 together. As depicted in FIGS. 2, 3 and 4, this may be achieved by using cross sectional shapes for inflow conduit 12 and outflow conduit 14 whereby the former is nested within an elongate trough 26 which is formed along the length of the latter (or vice versa).

Using existing technology in the silicon extrusion field, inflow conduit 12 and outflow conduit 14 are separately extruded in their desired cross-sectional shapes and then bonded along their lengths as correspond to the trans-abdominal segment 20 or the proximal segments 21 and 23 of catheter 10. Lengths of inflow conduit 12 and outflow conduit 14 distal to the boundaries of the trans-abdominal segment 20 are simply left not bonded.

Because inflow conduit 12 and outflow conduit 14 are wholly separate structures which are merely bonded along the length over which they must cooperatively define an acceptable cross-sectional shape for the entire catheter 10, there is no need whatsoever for a component which corresponds to T-joint as is used in the Ash catheter and which would introduce the aforementioned problems associated with using such a component and create an undesirably angular path to be followed in the transition from a trans-abdominal segment 20 to the converging fluid transport branches 22 and 24.

As such, the preferred embodiment employs a J configuration thereby allowing fluids to follow a substantially radial path in the transition from a trans-abdominal segment 20 to the converging fluid transport branches 22 and 24.

Figure 5:
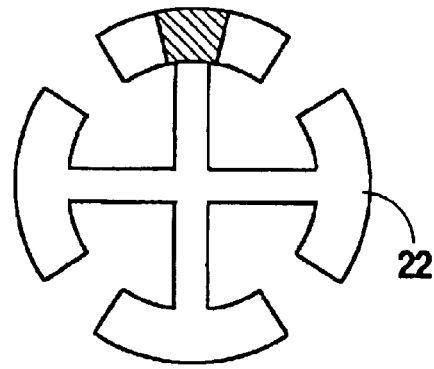
FIG. 5 is an elevational cross-section view of fluid transport branch 22 along line E—E of FIG. 1.
Figure 6:
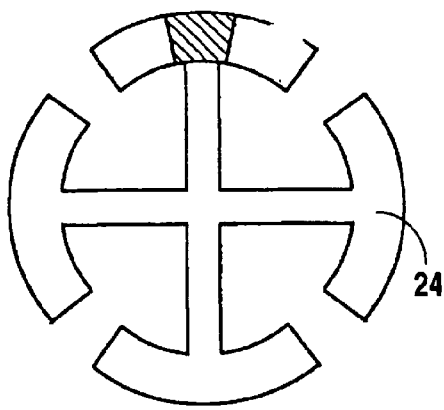
FIG. 6 is an elevational cross-section view of fluid transport branch 24 along line F—F of FIG. 1.
Figure 7:
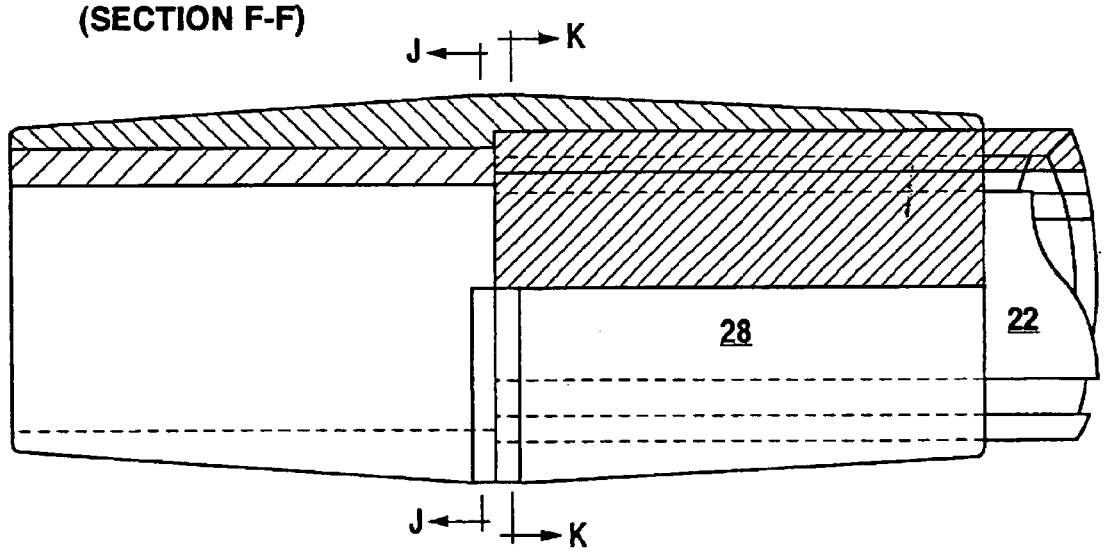
FIG. 7 is an elevational, partially cut away view of the juncture between input conduit 12 and fluid transport branch 22 bounded by juncture sleeve 28.
Figure 8:
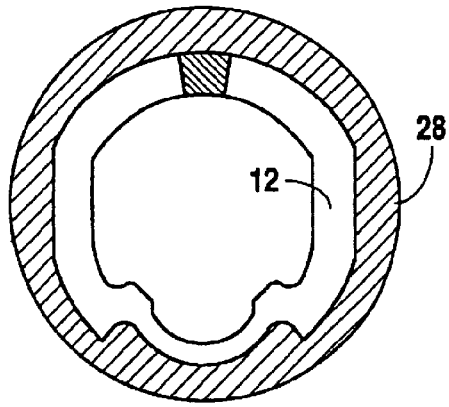
FIG. 8 is an elevational cross-section view of FIG. 7 along line J—J.
Figure 9:
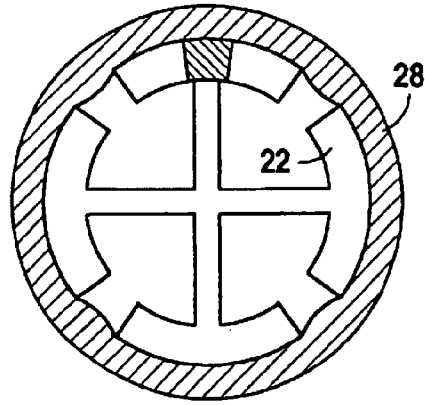
FIG. 9 is a cross-section view of FIG. 7 along line K—K.

FIGS. 5 and 6 depict exemplary cross-sectional structures for fluid transport branches 22 and 24 such that fluid transport branches 22 and 24 fall within the definition of fluted catheter segments as are known to be highly beneficial and avoiding omentum occlusion after implantation. While the cross sectional configuration depicted in FIG. 5 for fluid transport branches 22 and 24 is a very good, if not the preferred configuration, such is only one of many fluted catheter segment configurations which may be incorporated into any embodiment of the present invention, the specific configuration of the fluted segments not being a critical element of the present invention.

Referring principally to FIGS. 1, 7, 8, and 9, distally of distal divergence point 18 inflow conduit 12 and outflow conduit 14 each are mated with their respective fluid transport branches 22 and 24 for use of juncture sleeves 28. Variations of this juncture scheme to accommodate differing geometries for the inflow or outflow conduits, as well as for the fluid transport branches, will be apparent to persons skilled in the art. In any event, however, the juxtaposition of conduits 12 or 14 and fluid transfer branches 22 or 24 will result in substantially a coaxial arrangement whereby no angular deviation from either conduit and its respective fluid transport branch.

Implantation of catheter 10 of the present invention is ideally achieved through the same methodology taught by Ash beginning in column 5, line 27 and ending at Column 6, line 8, which portion of said patent (U.S. Pat. No. 5,322,519) is incorporated herein by reference.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A peritoneal dialysis catheter comprising:

an elongate inflow conduit having a first elongate juxtaposition surface residing on a first medial segment of the exterior surface of said elongate inflow conduit, a first distal segment lying distal of said first medial segment, and a first proximal segment lying proximal of said first medial segment;

an elongate outflow conduit having a second elongate juxtaposition surface residing on a second medial segment of the exterior surface of said elongate outflow conduit, a second distal segment lying distal of said second medial segment, and a second proximal segment lying proximal of said second medial segment;

said elongate inflow conduit and said elongate outflow conduit being respectively contoured whereby a juxtaposition consisting essentially of said first elongate juxtaposition surface and said second elongate juxtaposition surface along their respective said first and second medial segments results in the joint formation of a structure, the cross sectional contour of which is substantially circular and substantially free of peripheral gaps or spaces;

said elongate inflow conduit and said elongate outflow conduit being bonded in said juxtaposition along respective said medial segments and remaining un-bonded along their respective said first and second distal segments; and where said medial portion and said exterior portion form an acute angle with respect to one another at a transition portion.

2. The peritoneal dialysis catheter of claim 1, where said transition portion follows a substantially radial path.

* * * * *